(12) United States Patent
Torgerson

(10) Patent No.: US 10,835,645 B2
(45) Date of Patent: Nov. 17, 2020

(54) HIGH TENACITY FIBERS

(71) Applicant: RxFiber, LLC, Santa Rosa, CA (US)

(72) Inventor: Robert D. Torgerson, Narragansett, RI (US)

(73) Assignee: RxFiberLLC, Santa Rosa, CA (US)

( * ) Notice: Subject to any disclaimer, the term of this patent is extended or adjusted under 35 U.S.C. 154(b) by 53 days.

(21) Appl. No.: 15/998,321

(22) Filed: Aug. 3, 2018

(65) Prior Publication Data

US 2019/0125939 A1    May 2, 2019

Related U.S. Application Data

(63) Continuation of application No. PCT/US2017/016602, filed on Feb. 3, 2017.

(60) Provisional application No. 62/291,866, filed on Feb. 5, 2016.

(51) Int. Cl.
| | | |
|---|---|---|
| *A61L 31/16* | (2006.01) | |
| *A61L 17/06* | (2006.01) | |
| *A61L 29/14* | (2006.01) | |
| *A61L 31/06* | (2006.01) | |
| *A61L 17/10* | (2006.01) | |
| *A61L 29/06* | (2006.01) | |

(52) U.S. Cl.
CPC .............. *A61L 31/16* (2013.01); *A61L 17/06* (2013.01); *A61L 29/148* (2013.01); *A61L 31/06* (2013.01); *A61L 17/105* (2013.01); *A61L 29/06* (2013.01)

(58) Field of Classification Search
None
See application file for complete search history.

(56) References Cited

U.S. PATENT DOCUMENTS

| | | | | |
|---|---|---|---|---|
| 5,349,028 | A * | 9/1994 | Takahashi | B32B 27/10 428/395 |
| 6,352,948 | B1 * | 3/2002 | Pike | B32B 5/02 442/361 |
| 7,758,952 | B2 * | 7/2010 | Paris-Jolly | A61L 2/26 428/292.1 |
| 8,747,468 | B2 * | 6/2014 | Martin | A61L 17/105 623/13.11 |
| 2005/0079093 | A1 * | 4/2005 | Cannady | B32B 7/05 422/1 |
| 2008/0147198 | A1 * | 6/2008 | Cherok | A61F 2/0063 623/23.72 |
| 2009/0148492 | A1 * | 6/2009 | Dave | A61B 17/0057 424/423 |
| 2010/0272938 | A1 * | 10/2010 | Mitchell | D21H 13/40 428/36.1 |
| 2013/0244521 | A1 * | 9/2013 | Jones | B32B 5/06 442/181 |
| 2013/0269294 | A1 * | 10/2013 | Benton | B32B 5/26 53/425 |
| 2013/0338791 | A1 * | 12/2013 | McCullen | A61L 27/38 623/23.72 |
| 2016/0166727 | A1 * | 6/2016 | Ganatra | A61L 17/105 424/1.11 |

\* cited by examiner

*Primary Examiner* — Nina Bhat
(74) *Attorney, Agent, or Firm* — McGurk Group LLC

(57) ABSTRACT

Medical grade yarns, medical devices constructed of such yarns, and methods for making such yarns and devices are described. Polyester drawn fibers, and more particularly high strength and high tenacity micro polyester fibers for use in medical devices, and methods of preparing the same are provided.

30 Claims, 8 Drawing Sheets

HIGH TENACITY FIBERS

BACKGROUND

1. Field

This disclosure relates to polyester drawn fibers, and more particularly to high strength and high tenacity polyester fibers for use in medical devices, and methods of preparing the same

2. Background

To date the USFDA (United States Food and Drug Administration) and other regulatory bodies have identified poly (ethylene terephthalate) or "polyester" fibers and yarns as an "approved" biomaterial for many different biomedical and surgical implantable applications. For historical reasons, regular tenacity polyester fibers, i.e., fibers and/or yarns with a tenacity of three to five grams per denier have always been preferred and readily available since the 1950's. Current polyester yarn is used in current medical devices, i.e. regular tenacity fibers, have been shown to break down in the body over a few years. Some studies have shown evidence of polyester chemical degradation over time which is believed to result in of strength in-vivo after implantation. It is believed that the loss of strength is due to both mechanical fatigue and chemical degradation. For example a significant loss in stich density of devices and loss in burst strength of devices over an 8 year period of time has been shown. Patients are living longer and bio-textile devices need to survive longer in the patient to mitigate surgical intervention. Accordingly, there is a need for a fiber and yarn for manufacturing medical devices that may be more stable in a biological environment, which will increase the survivability of the bio-textile devices.

SUMMARY

According to the invention a sterilized medical device is provided comprising a material constructed of a high tenacity micro fiber. The high tenacity micro fiber may have a denier per filament of less than 1.5 dpf (denier per filament), and a tenacity of from about 7.0 to 9.0 gram-force per denier. The material may have a fiber denier of equal or less than about 40.

The fiber may comprise a monofilament fiber. The monofilament fiber may have a denier per filament of from about 0.6 to about 1.5. The fiber may comprise a multifilament fiber. The multifilament fiber may have a denier per filament of from about 5 to about 40. The multifilament fiber may have an elongation of less than 15%.

The fibers of the device may be formed of a polymer material. The polymer may have a starting relative viscosity higher than 1.636 dl/g. The polymer may have a starting relative viscosity of about 1.995 dl/g to about 2.015 dl/g. The polymer may have a starting relative viscosity of about 1.9 dl/g to about 2.2 dl/g. The fibers may be formed of a polyester free of Titanium Dioxide. The fibers may be formed of a pure polyester.

The medical device may comprise a number or variety of device including but not limited to those listed below. The device may comprise a catheter. The device may comprise a tubular member. The tubular member may comprise a suture. The suture may have a linear density of greater than 1500 denier and a modulus (GPa—giga pascals) greater than 5.0. The device may comprise an implantable medical device.

The material of the device may comprise a low profile material having a fabric thickness of the fabric less than 0.002".

According to the invention a sterilized medical device may be provided comprising a material constructed of a micro high tenacity monofilament fiber having a denier per filament of from about 0.6 to 1.5 dpf (denier per filament), and a tenacity of from about 6.5 to 9.0 gram-force per denier.

According to the invention a medical grade yarn is provided comprising a plurality of fibers wherein each of the fibers comprises a high tenacity micro fiber. The high tenacity micro fiber may have a denier per filament of less than 1.5 dpf, and a tenacity of from about 7.0 to 9.0 gram-force per denier. Each of the fibers of the yarn may have a fiber denier of equal or less than about 40. The fibers of the yarn may comprise monofilament fibers. The monofilament fibers may have a denier per filament of from about 0.6 to about 1.5. The fibers of the yarn may comprise multifilament fibers. The multifilament fibers may have a denier of from about 5 to about 40. The multifilament fibers may have an elongation of less than 15%. The fibers may be formed of a polymer. The polymer may have a starting relative viscosity higher than 1.636 dl/g. The polymer may have a starting relative viscosity of about 1.995 dl/g to about 2.015 dl/g. The polymer may have a starting relative viscosity of about 1.9 dl/g to about 2.2 dl/g. The fibers may be formed of a polyester free of Titanium Dioxide. The fibers may be formed of a pure polyester.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

Figure 1:
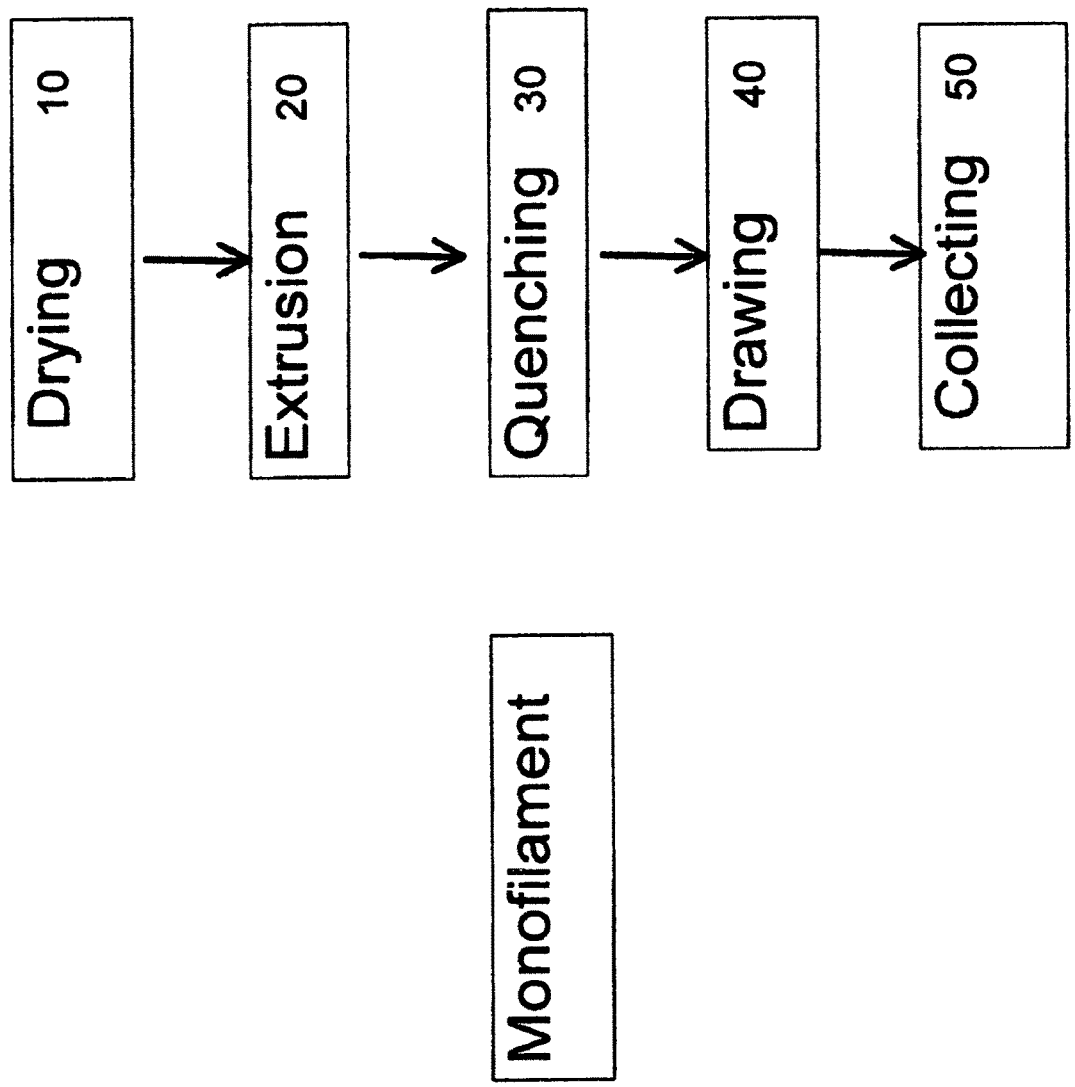
FIG. 1 is a flow chart depicting a method of manufacturing a monofilament of a fiber.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

The present invention may provide medical implants and/or devices comprising thinner high tenacity polyester yarn. It is believed that the fiber, yarn, material and devices of the present invention have a more stable crystalline structure for long term implant. The present invention provides reduced profile of bio-textile devices in particular to facilitate implant in medical applications. A lower profile may also facilitate easier folding and loading into a delivery catheter as well as easier deployment. The present invention may further provide finer yet stronger and more flexible high tenacity polyester sutures and such braided sutures with improved knot security when compared to current regular tenacity polyester sutures.

The present disclosure is directed to a micro high tenacity having a denier per filament of less than 1.5, a fiber denier of less than 40, and a tenacity of from about 7.0 to about 9 gram-force per denier. In some embodiments, the fiber may be configured to produce fabric structures such as a braid, a weave or a knit. In some embodiments, the structures may be used in a medical device, such as a trans catheter device. In some embodiments, the fiber may aid in longevity and durability of the medical devices. In some embodiments, the fiber may provide the device with a maintained integrity and may reduce a profile of the medical device for ease of deliverability.

In some embodiments in accordance with the present disclosure, a high tenacity, low denier fiber is provided. In some embodiments, the fiber are formed from pure polyester or polyester free of Titanium Dioxide. In some embodiments, the fiber may be a monofilament. In some embodiments, the fiber may be a multifilament. In some embodiments, the monofilament may have a denier per filament of from 0.6 to 1.5. In some embodiments, the monofilament may have a denier of less than 1.5. In some embodiments, the multifilament may have a total denier of less than 40. In some embodiments, the multifilament may have a denier of from about 5 to about 40. In some embodiments, multifilament fibers of the present disclosure may have a tenacity from about 7.0 gram-force per denier to about 9 gram-force per denier. In some embodiments, monofilament fibers of the present disclosure may have a tenacity from about 6.5 gram-force per denier to about 9 gram-force per denier.

In some embodiments, a multifilament fiber has a tenacity of at least 7.0 gpd (grams per denier), elongation of less than 15% and a denier of equal to or less than 40 for a multifilament fiber. In some embodiments, a monofilament fiber has a denier per filament from 0.6 to 1.5, and a tenacity of at least 6.5 gpd. The multifilament and/or monofilament fibers may be made using a coupled extrusion process that directly affects the properties of the fibers while they are processed.

According to aspects of various embodiments, a high tenacity polyester yarn is provided which is believed to have improved mechanical properties with respect to previously used materials, particularly those used in medical or biomedical applications. The inventions described herein are believed to have a number of advantages over the current regular tenacity polyester yarn in certain biomedical (biotextile) applications. A high tenacity fiber as used herein means the breaking strength of the fiber (in units of grams) divided by the denier of the fiber as per ASTM 2256 of about 7.0 to 9.0 gpd for a multifilament fiber and about 6.5 to 9.0 gpd for a monofilament fiber. High tenacity micro fibers are defined herein to mean high tenacity fibers that have sizes of about 0.6 dpf and 1.5 dpf.

According to aspects of the inventions, it is believed that a thinner, high tenacity polyester yarn as described herein may provide a more stable crystalline structure for long term implant and may reduce the profile of bio-textile devices. The lower profile may also facilitate easier folding and loading into the delivery catheter as well as easier deployment. It may also be possible to braid finer yet stronger and more flexible HT polyester sutures with improved knot security compared to current regular tenacity polyester sutures. It is also believed that the high tenacity yarn of the invention may retain a higher strength after some sterilization techniques than fibers or yarns traditionally used in medical applications.

The high tenacity fiber in a suture form demonstrated that for strength to diameter it only takes two-thirds of regular tenacity fiber resulting in a thinner wall device.

The invention may provide, a method for producing a micro high tenacity (monofilament or multifilament) fiber comprises melt-spinning pure polyester to form a fiber and drawing the fiber to a desired ratio.

The invention may provide a product, device, or medical device as described herein manufactured using the method described above.

Referring to FIG. 1, the present disclosure provides a method of producing a high tenacity polymer monofilament fiber. A "micro filament," as used herein, shall refer to a single filament made from the polymer and that is in the range of about 0.6 to 1.5 deniers per filament. The method may comprise step 10 of drying a source polymer, step 20 of extruding the polymer through a die with an extruder to form an extruded monofilament, step 30 of quenching the extruded monofilament, step 40 of drawing the extruded monofilament through a series of godets, and step 50 collecting the extruded monofilament on to a winder. In some embodiments, the method may be a coupled process combining the spinning (extrusion and quenching) and drawing to form a final wound microfilament fiber.

In some embodiments, the starting material is pure polyester (high tenacity) polymer that does not have any contaminants or colorants in it to inhibit polymer chains or molecular weight of the polymer. In particular, in some embodiments, the starting polyester of the present disclosure is free of titanium dioxide (a colorant commonly present in polyester polymers). In some embodiments, the polymer may have a starting relative viscosity higher than 1.636 dl/g. In some embodiments, the starting relative viscosity may be from about 1.995 dl/g to about 2.015 dl/g. In some embodiments, the starting polymer may be from about 1.9 dl/g to about 2.2 dl/g. The starting material may be provided in the form of pellets or any other shapes conventionally used in the art.

In the drying step 10, the starting material can be dried for about 12 hours. In some embodiments, the drying step 10 may be from about 2 to about 24 hours. In some embodiments, the drying step may be more than 12 hours. In some embodiments, the drying step 10 may occur at a temperature of between 100° C. and 160° C., until a moisture level of the fiber ends up between 0% and 0.001%. The drying step can be carried out in a conventional heated pellet dryer or a similar device.

In the extruding step 20, a conventional extruder may be employed for melt-spinning the polymer into a quenching bath to form a monofilament fiber. In some embodiments, the temperature of the extruder may range from 240° C. to 260° C. but may be dependent on the type of the extruder. In some embodiments, the temperature may range from 240° C. to 250° C. In some embodiments, the extruder may comprise a die with a length/diameter (L/D) ratio of 2:1 or 4:1.

In the quenching step 30, the monofilament fiber may be vertically or horizontally quenched. The quenching 30 may take place in a water bath. In some embodiments, the water may be free of contaminants (e.g. distilled or otherwise purified water). In some embodiments, other fluids may be used as long as such fluids are safe and do not contaminate the fiber.

In the drawing step 40, the monofilament fiber is collected from the quenching bath and is drawn on a series of godets having a varying speed. In some embodiments, the series of godets may comprise at least 3 godets. In some embodiments, the series of godets may comprise from 3 to 5 sets of godets. In some embodiments, the sets of godets may have a draw ratio of at least 3.5. In some embodiments, the draw ratio is from 3.5 to 6.5. In some embodiments, the draw ratio is from 4.0 to 4.5. As used herein, "draw ratio" shall mean the speed of the final godet set divided by the speed of the initial godet. In some embodiments, the speed of the godets may be from about 900 meters per minute to about 1100 meters per minute. In some embodiments, the speed may be from about 500 to about 1500 meters per minute.

In some embodiments, at least some of the godets in the series of godets may be heated. Heat may soften the polymer to allow it to be drawn or oriented by being around a glass transition of the polymer. For monofilaments, the godets may be used to keep the monofilament moving along a process line, while using hot air dryers as a heat mechanism to draw the monofilament fiber with the varying speed of the godets. The heated godets may be heated to a common temperature, or the heated godets may be heated to different temperatures. In some embodiments, the godets may range in temperature between room temperature (about 21° C.) to about 200° C. In some embodiments, instead of heating the godets, a hot air dryer may be used, heating the monofilaments to temperatures ranging from about 100° C. to about 200° C. as the monofilaments are larger in diameter and need to maintain constant temperature during drawing to keep the monofilament from cracking or breaking.

In the collecting step 50, a winder may be employed to collect the drawn fiber from the godets. In some embodiments, the take-up speed of the winder may be the same speed as the speed of the last godet. In this manner, the winder can keep constant tension on the fiber prior to winding, so as to mitigate any inconsistent fiber properties.

Figure 2:
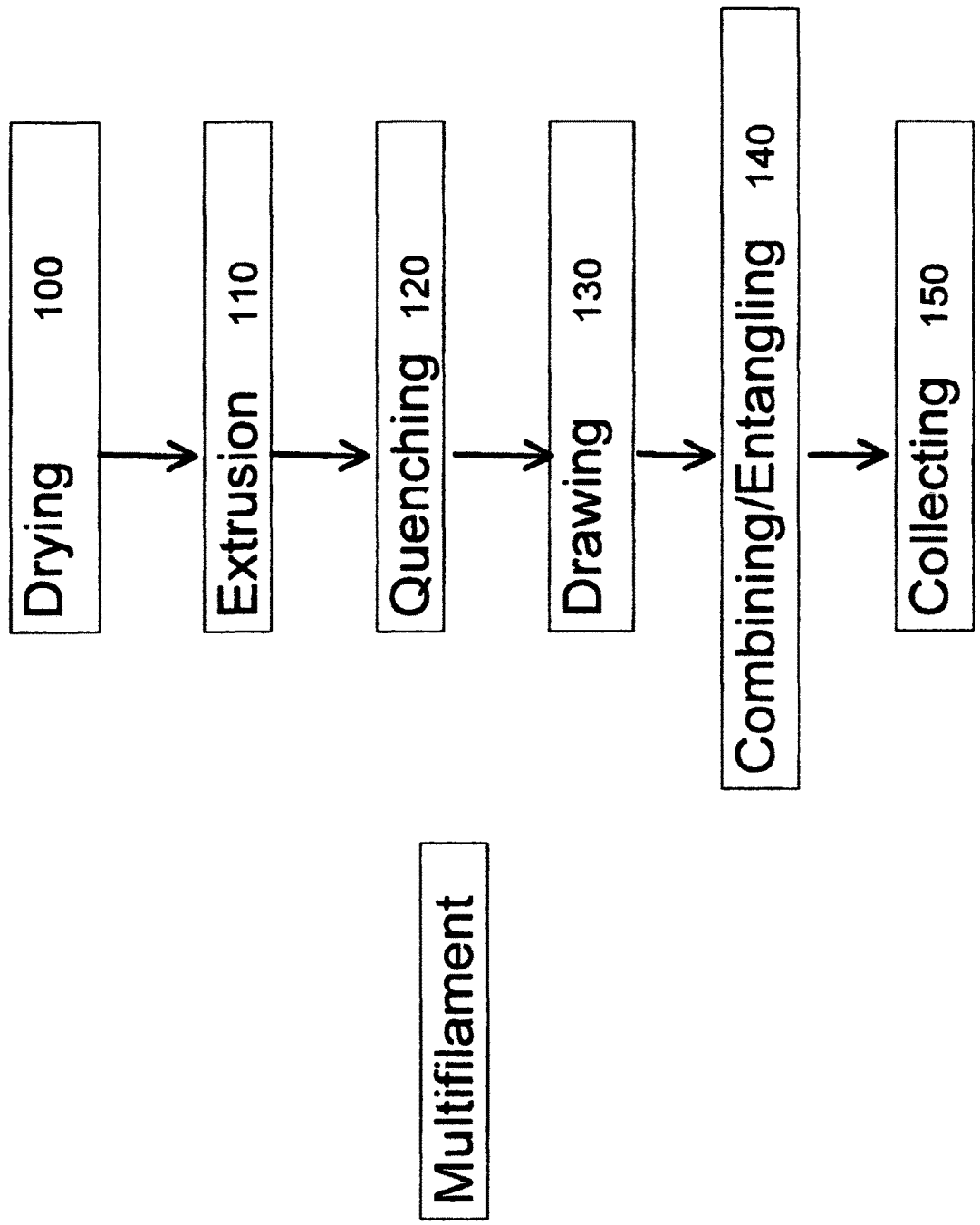
FIG. 2 is a flow chart depicting a method of manufacturing a multifilament of a fiber.

Referring to FIG. 2, the present disclosure provides a method of producing a high tenacity polymer multifilament fiber. A "multifilament" shall refer to a fiber comprising a plurality of microfilaments. The method may include step 100 of drying a starting polymer, step 110 of extruding the polymer through a die with an extruder to form a plurality of extruded monofilaments, step 120 of quenching the extruded monofilaments, step 130 of drawing the extruded monofilaments through a series of godets in a draw station, step 140 of combining or entangling the extruded monofilaments to form a multifilament, and step 150 of collecting the multifilament on a winder. In some embodiments, the method may be a coupled process combining the spinning (extrusion and quenching) and drawing to form a final wound multifilament fiber.

In some embodiments, the starting material is pure polyester (high tenacity) polymer that does not have any contaminants or colorants in it to inhibit polymer chains or molecular weight of the polymer. In particular, in some embodiments, the starting polyester of the present disclosure is free of titanium dioxide (a colorant commonly present in polyester polymers). In some embodiments, the polymer may have a starting relative viscosity higher than 1.636 dl/g. In some embodiments, the starting relative viscosity may be from about 1.995 dl/g to about 2.015 dl/g. In some embodiments, the starting polymer may be from about 1.9 dl/g to about 2.2 dl/g. The starting material may be provided in the form of pellets.

In the drying step 10, the starting material is dried for about 12 hours. In some embodiments, the drying step 10 may be from about 2 to about 24 hours. In some embodiments, the drying step may be more than 8 hours. In some embodiments, the drying step 10 may occur at a temperature of between 100° C. and 160° C. such that a moisture level of the fiber ends up between 0% and 0.001%. The drying step can be carried out in a conventional heated pellet dryer or a similar device.

In the extruding step 110, a conventional extruder may be employed for melt-spinning the polymer into a quenching bath to form a fiber. In some embodiments, the temperature of the extruder may range from 260° C. to 304° C. In some embodiments the extruder may have a larger diameter with more heads (dies) operating at higher temperatures. In some embodiments, the extruder may comprise a die with a length/diameter (L/D) ratio of 2:1 or 4:1. Because multifilaments may be oriented right out of the die, a heated collar may he used to help with the initial vertical drawing out of the die face and reduce multifilament breaks. The collar may be close to or in contact with the die exterior of the die. In some embodiments the heated collar may be heated with a temperature range from 100° C. to 250° C. In some embodiments, the heated collar may just act as an insulation barrier not allowing cool room air blow across the face of the die, which will cool the fibers too fast. If the fiber cools too fast initially out of the die the fibers will not draw and end up breaking (a non continuous fiber).

In the quenching step 120, the fiber may be vertically or horizontally quenched. In some embodiments, the extruder may be above the quenching bath, and as the multifilament fibers come out of the die, gravity is used to allow the fibers to fall to the draw station. Room temperature air may be used for quenching 120. In some embodiments, the fibers may pass from the die into a tube that is configured to keep air movement from blowing on the fibers too much. The tube helps control feeding of the multifilament fibers from the die face to the lube godet. In some embodiment, the fiber may be quenched using air at a temperature between 21 to 250° C. In some embodiments, the fiber may be quenched using an inert gas such as nitrogen, or other fluid as long as such fluid is safe and does not contaminate the fiber.

During the quenching step 120, a spin finish may be applied to the extruded filaments. The spin finish can be applied (1) to keep the individual filaments together while they are drawn, (2) to reduces the friction of the fiber on the godets, and (3) so that when the fiber is made into a fabric structure (braid, weave or knit) friction in that process is reduced or the combination thereof. In some embodiments, a water soluble spin finish is used to minimize friction or drag as the fiber comes in contact with surfaces during processing, which can be washed off after the braid, weave or knit structure has been created.

In the drawing step 130, the fiber is collected from the quenching bath and is drawn on a series of godets having a varying speed. In some embodiments, the series of godets may comprise at least 3 godets, including a lube godet set, a second godet set and a third godet set. In some embodiments, the series of godets may comprise from 3 to 5 sets of godets. In some embodiments, the sets of godets may have a draw ratio of at least 3.5. In some embodiments, the draw ratio is from 3.5 to 6.5. In some embodiments the draw ratio is from 4.0 to 4.5. In some embodiments, the speed of the godets may be from about 250 meters per minute to about 1800 meters per minute. In some embodiments, the speed may be from about 200 to about 2500 meters per minute.

In some embodiments, at least some of the godets in the series of godets may be heated. The heated godets may be heated to a common temperature, or the heated godet may be heated to different temperatures. In some embodiments, the godets may range in temperature between about 75° C. to about 250° C. The heat softens the polymer to allow it to be drawn or orientated by being around the glass transition of the polymer. This process relies on the heat from the godets to draw the fiber. In some embodiments, the temperature may range from 85° C. to about 200° C. In some embodiments, the lube godet set may have a temperature of from 75° C. to 95° C., the second set of godets may have a temperature of from 95 to 150° C. and the third set of godets may have a temperature of from 150 to 250° C.

In the combining step 140, the individual monofilaments are collected from the godets and are combined together to form a multifilament fiber. In some embodiments, the individual monofilaments are passed through an air entanglement system to bind the individual monofilaments together to form the multifilament fiber. In some embodiments the multifilament fibers can be collected by the winder (take-up) without being air entangled.

In the collecting step 150, a winder may be employed to collect the multifilament fiber onto a spool. In some embodiments, the take-up speed of the winder may be slower than the speed of the last godet. In this manner, the multifilament fiber may be kept relaxed prior to winding so that the tension is not too high where the fiber cannot be air entangled or has breaks in the individual monofilaments, and so that the tension is not too low where the filaments will balloon causing broken filaments. If the tension is too high during collecting 150 onto the spool, the polymer will relax on the spool either crushing the spool or breaking filaments.

Figure 3:
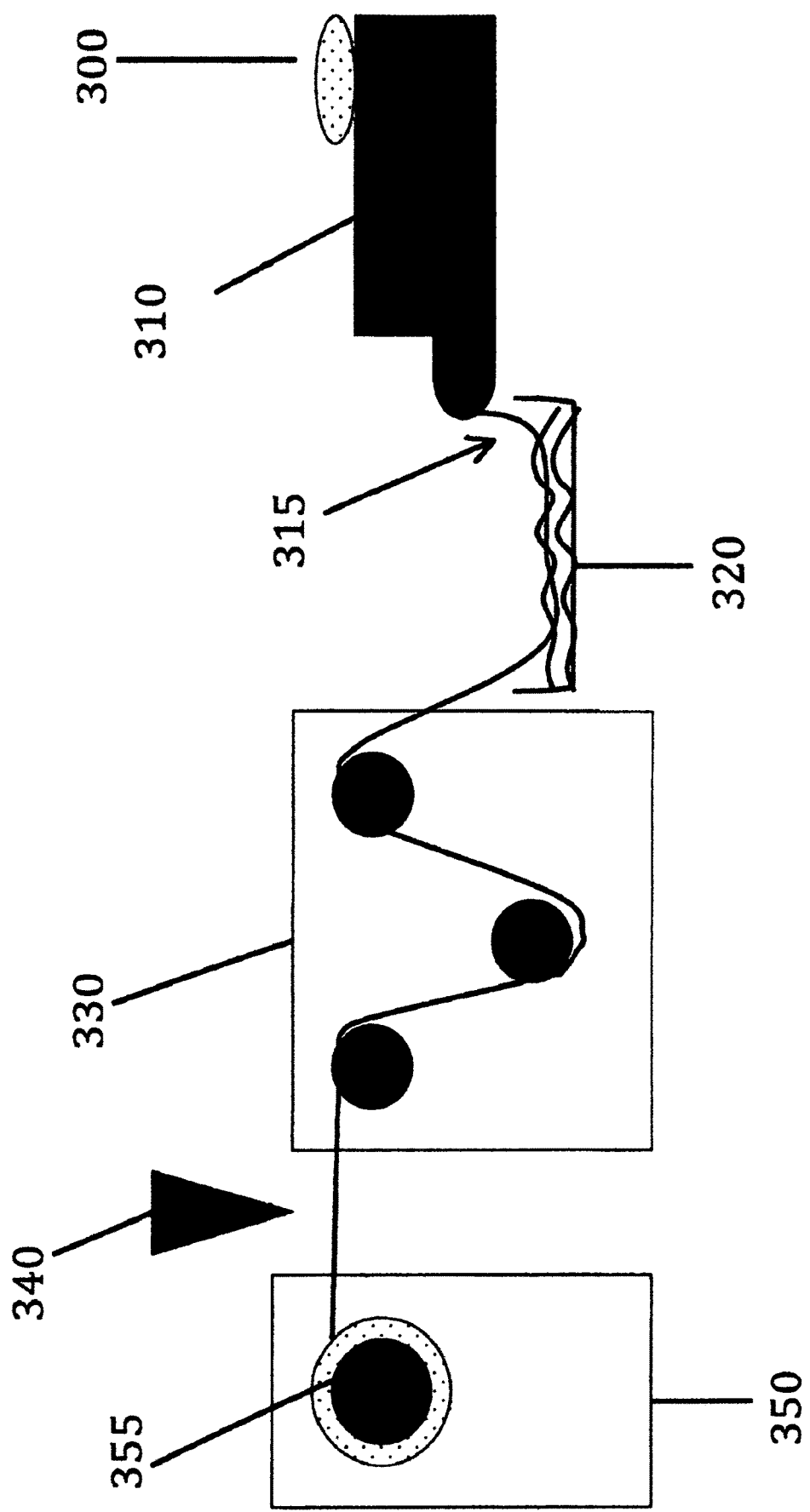
FIG. 3 illustrates a coupled spinning and drawing process.

In reference to FIG. 3, an exemplary equipment set up for carrying out the processes for producing fiber according to the present disclosure is illustrated. As described above, the starting pure polyester 300 may be added to an extruder 310. The extruder 310 may extrude the starting material 300 in the form of one or more filaments 315 into a quenching bath 320. The filaments 315 may be collected from the quenching bath 320 and drawn using a series of godets 310. In case of a monofilament fiber, the drawn filaments 315 may be collected on a spool 355 by a winder 350. In case of a multifilament fiber, the drawn filaments 315 may be passed through an entanglement system 340 to form a multifilament fiber, which can then be collected on a spool 355 of a winder 350. It should be noted that other equipment as known in the art may also be used in addition or instead of the equipment shown in FIG. 3.

According to some aspects, monofilament and multifilament fibers may be utilized to produce fabric or mesh structures used for fabricating of medical devices or other materials. The fibers of the present disclosure may be braided, knitted, or woven to produce the fabrics. In some embodiments, the fibers may be used to produce a braided suture. According to some embodiments of the invention, a medical device fabric is provided constructed of the monofilament or multifilament fibers described herein wherein the fabric is sterilized and wherein properties of the fibers or material are similar to those prior to sterilization, i.e., wherein the process of sterilization does not significantly impact the properties of the fiber. The outcome is believed to demonstrate a better performing fabric for the device to ensure longevity of the product within the body.

Figure 5:
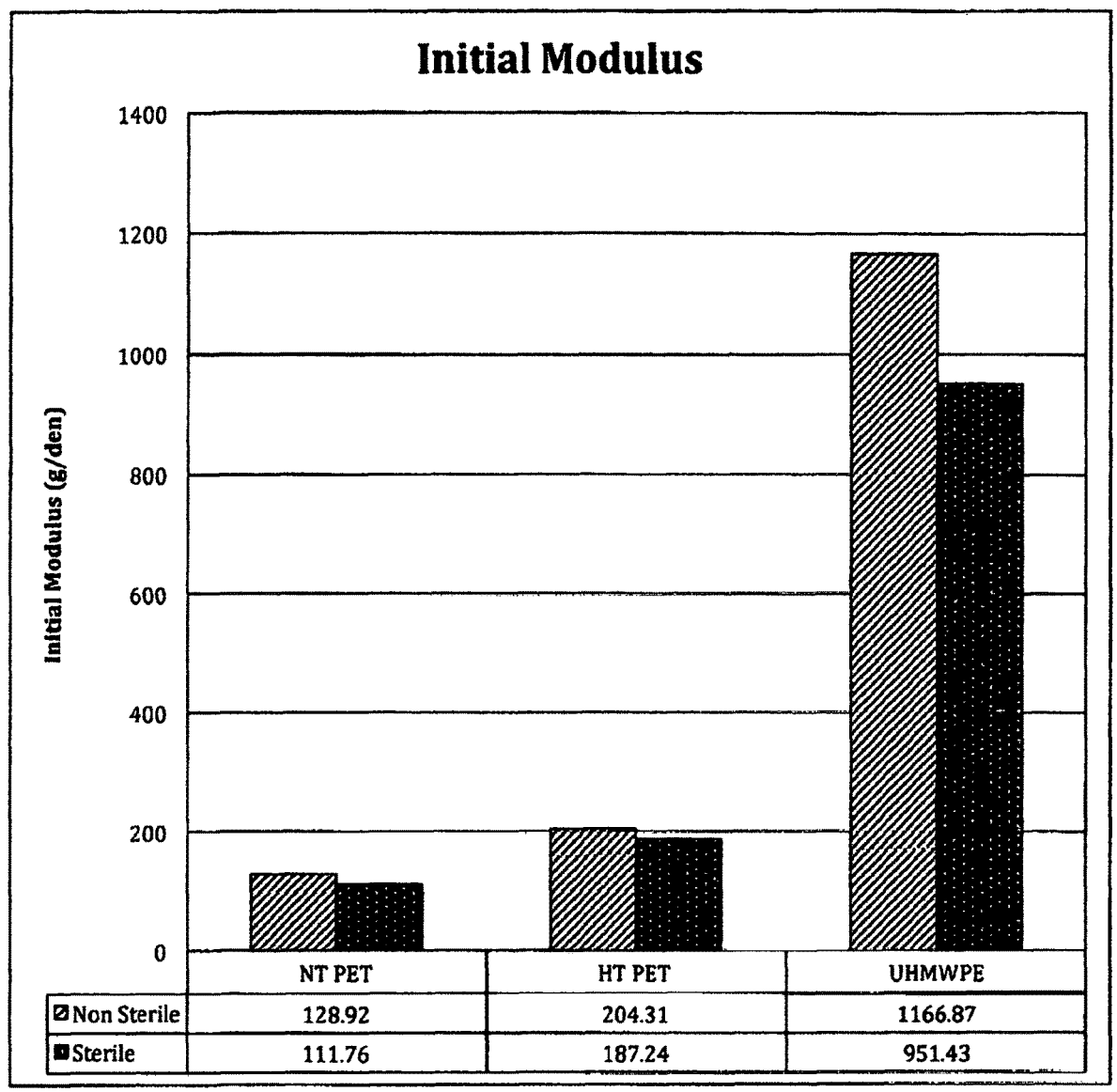
FIG. 5 illustrates a comparison of Modulus of sutures of Example 1.

The monofilament and multifilament fibers of the present disclosure may be used in connection with fabricating a medical device. In some embodiments, the fibers may aid in longevity and durability of the medical device. In some embodiments, the fibers may provide the device with a maintained integrity and may reduce a profile of the medical device for ease of deliverability. In some embodiments, monofilament and multifilament fibers of the present disclosure may be utilized to produce fabric structures having various designs as seen in FIG. 5. In some embodiments, the fiber may aid in longevity and durability of the medical devices. In some embodiments, the fiber may provide the device with a maintained integrity and may reduce a profile of the medical device for ease of deliverability. According to some embodiments a sterilized implantable medical device is provided constructed of a fabric form of the fibers described above which may be formed using one of the methods described with respect to FIGS. 1-3.

Figure 6:
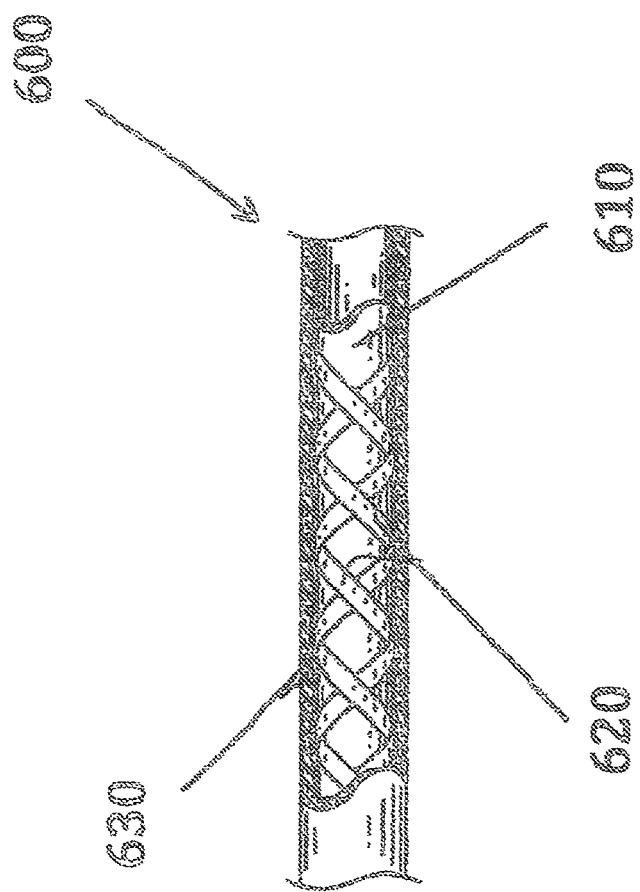
FIG. 6 depicts a catheter comprising a layer of fibers of the present disclosure.
Figure 7:
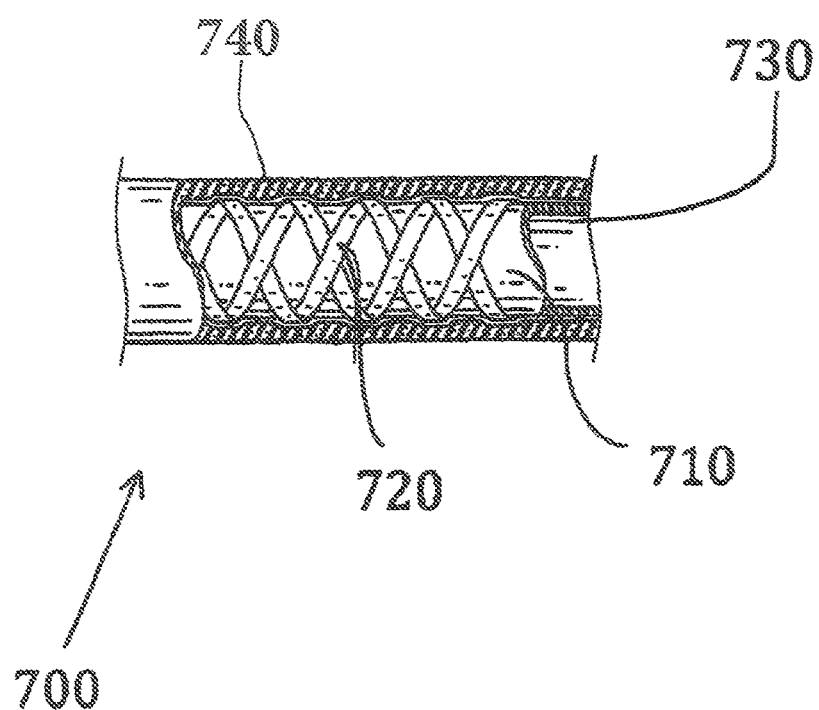
FIG. 7 depicts an implantable medical device constructed from fibers of the present disclosure.

In some embodiments a tubular medical device is provided. In some embodiments the tubular medical device is a hollow tubular medical device. In some embodiments, the tubular medical device comprises a sheath material constructed of a high tenacity fiber or yarn of the invention as described with respect to various embodiments thereof, herein. In some embodiments, the tubular medical comprises an implantable tubular medical device. In some embodiments the medical device comprises a low profile medical device constructed at least in part of the high tenacity yarn or fiber described herein. A low profile material may comprise a fabric having a fabric thickness of less than 0.002". Low profile materials may be used to construct a low profile device in accordance with the invention which may include, but is not limited to, a device that can be loaded into a smaller diameter delivery system and deployed into the body through a variety of access points—brachial, femoral, apical, etc. In some embodiments the medical device, for example, any of the devices described herein or using a fiber or yarn, comprises a high tenacity fiber or yarn as defined herein that is sterilized. In some embodiments, the medical devices may comprise cardiovascular devices such as Transcatheter Aortic-Valve Implantation (TAVI), Transcatheter Aortic-Valve Replacement (TAVR), aortic heart valve sewing rings, aortic heart valve fabric, mitral valve components, annuloplasty rings, cardiovascular patches, embolic protection devices, vascular grafts, coronary artery bypass grafts, and stent grafts. In some embodiments, the medical devices may comprise endovascular devices such as Tapered endovascular grafts Endovascular Aneurysm Repair (EVAR), Abdominal Aortic Aneurysm (AAA) Stent grafts, and Thoracic Aortic Aneurysm (TAA) Stent grafts. In some embodiments, the medical devices may comprise peripheral vascular devices such as vascular grafts, artificial blood vessels, and embolic protection devices. In some embodiments, the medical devices may comprise orthopedic and spinal devices such as artificial ligaments, artificial tendons, long bone fixation devices, spinal stabilization, containment devices, tethers, prosthetic ligaments, and casting tape. In some embodiments, the medical devices may comprise gynecological or urological devices such as pelvic floor repair mesh, incontinence slings, hernia mesh, prolapse repair slings, surgical mesh, abdominal wall patches, umbilical tapes, and erectile dysfunction devices. In some embodiments, the medical devices may comprise general surgery devices such as artificial ligaments, artificial tendons, long bone fixation devices, spinal stabilization devices, containment devices, tethers, prosthetic ligaments, and casting tape. In some embodiments, the medical devices may comprise wound care devices such as advanced dressings, tissue engineering scaffolds, and bio-absorbable scaffolds. In some embodiments, the medical devices may comprise neuro or tissue growth devices such as nerve regeneration conduits tubes, tissue engineering scaffolds, and stem cell platforms. Examples of devices are shown in FIGS. 6 and 7. These while showing some specific features, these examples are not intended to limit medical devices according to the invention which are constructed at least in part of high tenacity micro fibers described herein.

As depicted in FIG. 6, in some embodiments, the monofilament or multifilament fibers of the present disclosure may be used to form a catheter, such as a trans-catheter. In some embodiments, a catheter 600 may comprise an inner liner 610 with a lumen, a layer of microfilaments or multifilament fibers of the present disclosure 620 braided or woven around the inner liner to provide support for the inner liner, and a flexible polymer outer sleeve 630 melted over the fiber layer 620. By using less fabric to make the filament layer, the cross section of the catheter may be reduced, allowing for a reduction in a diameter of the catheter delivery system, which allows the catheter to be delivered into smaller anatomy or vessel diameters.

As depicted in FIG. 7, in some embodiments, the monofilament or multifilament fibers of the present disclosure may be used to form an implantable medical device, such as a stent-graft 700. In some embodiments, the stent graft 700 may comprise a lumen 710, and a support structure 720 with a liner 730 comprising a layer 740 of microfilaments or multifilament fibers of the present disclosure positioned around the support structure 720. By using less fabric to make the filament layer, the thickness of the walls of the stent-graft may be reduced, allowing for a lower profile of the stern graft to allow the stent graft to be loaded into a smaller diameter delivery system that can be inserted into smaller orifices or access to patient's vessels.

According to another aspect of the invention, sutures may be provided constructed of the materials described herein and that may be produced as set forth with respect to FIGS. 1-3.

EXAMPLES

Example 1

Figure 4A:
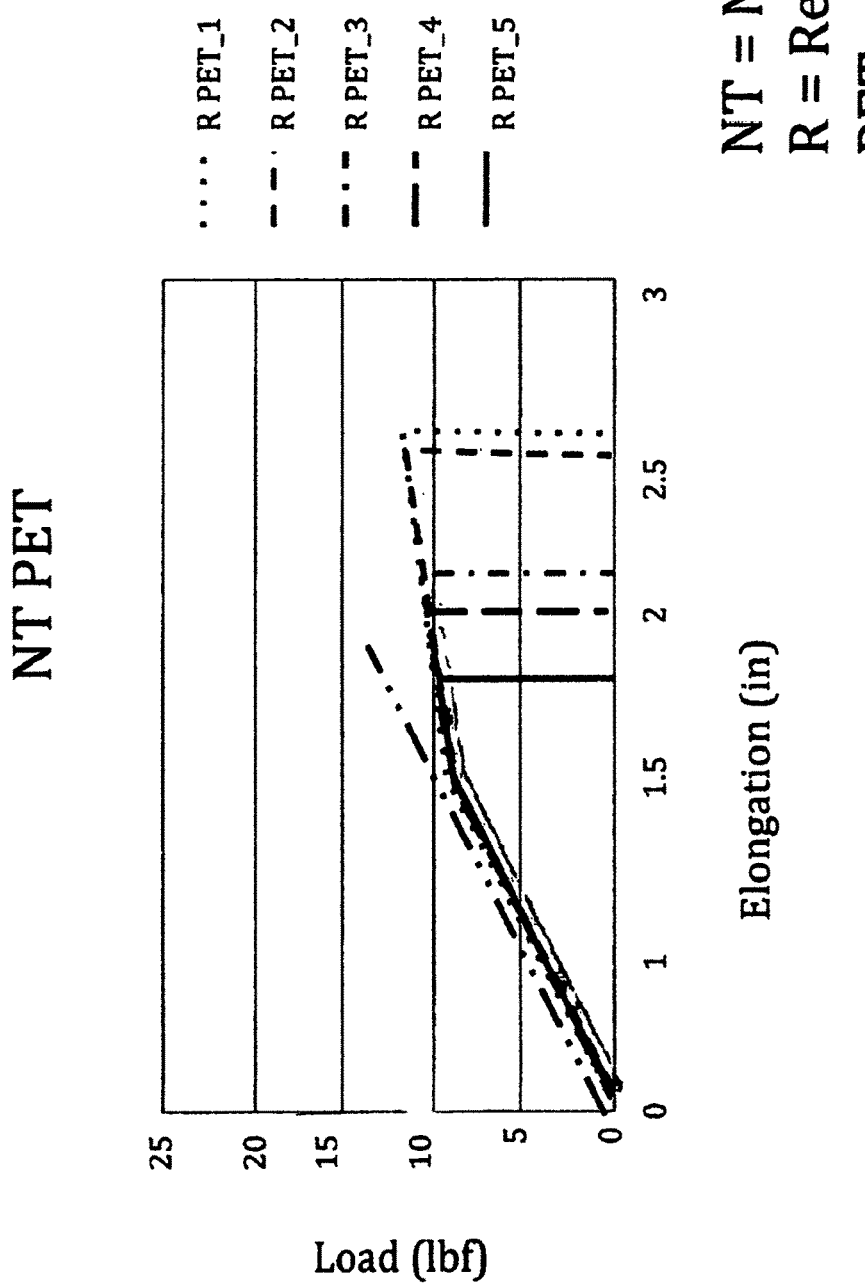
FIGS. 4A and 4B illustrate a comparison of strengths of sutures made with a normal tenacity (FIG. 4A) and a higher tenacity (FIG. 4B).
Figure 4B:
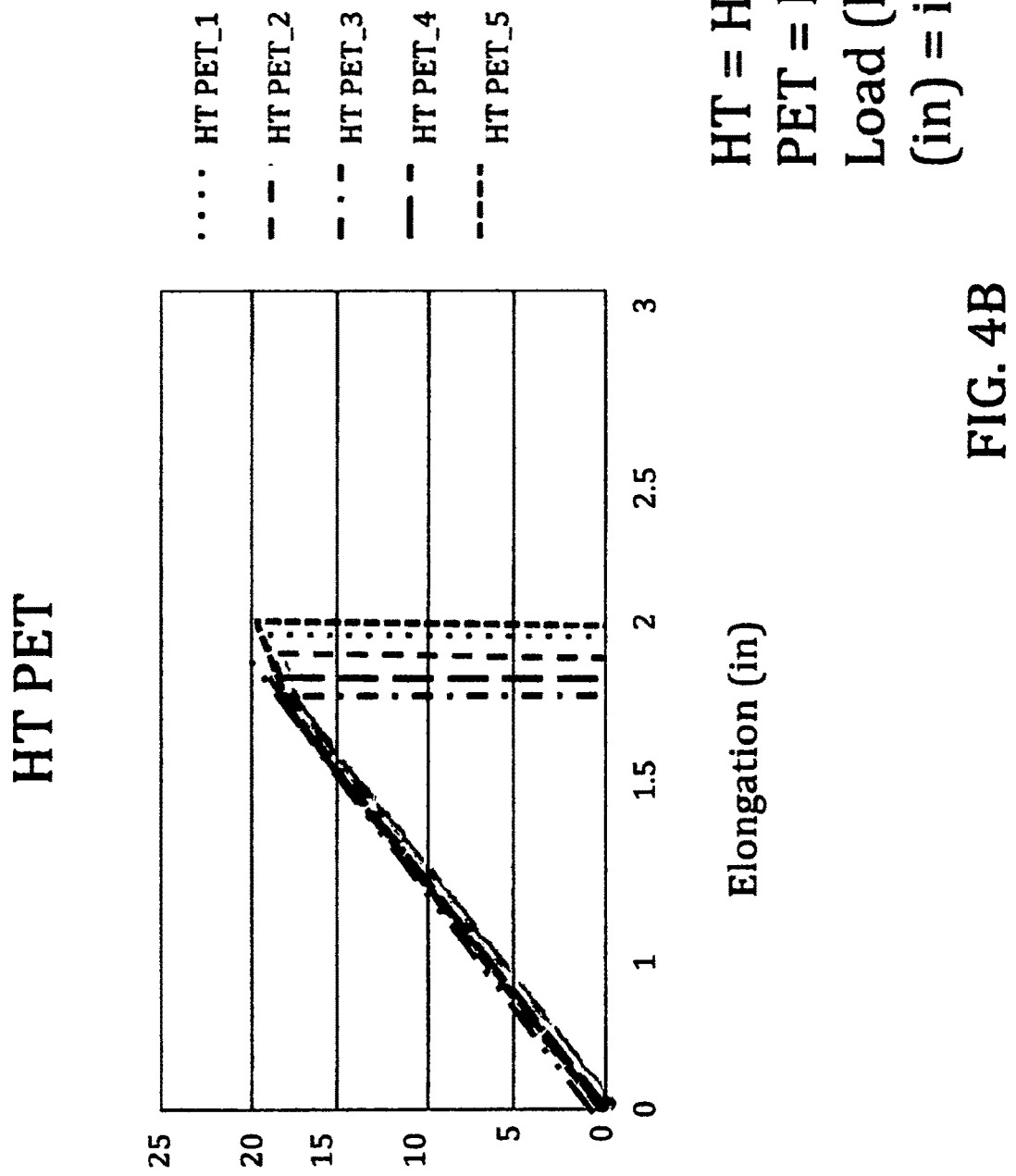

In this example, various fibers were braided into size 0 suture structures. A comparison was conducted using normal tenacity polyester braided suture, a high tenacity material braided suture and an UHMWPE (ultra high molecular weight polyethylene) braided suture. FIGS. 4A and 4B, describe the mechanical testing of a size 0 suture created using a normal tenacity (NT) polyester yarn of 40d and compared to a size 0 suture made using a high tenacity (HT) polyester yarn of 40d. The suture was made using a 16 carrier braider and each material was made using the same equipment and conditions to control the inputs. Table 1 below shows various properties of the sutures.

TABLE 1

|  | NT PET | High Tenacity | UHMWPE |
| --- | --- | --- | --- |
| Diameter (mm) | 0.312 | 0.359 | 0.392 |
| Approximate Suture Size | 0 | 0 | 0 |
| Suture Linear Density (denier) | 1350 | 1665 | 1215 |
| SutureTenacity (gf/den) | 3.67 | 5.25 | 13.99 |
| Modulus (GPa) | 4.34 | 5.52 | 30.37 |
| Tm (° C.) | 253.2 | 257.3 | 147.1 |
| $\Delta H_m$ (J/g) | 57.38 | 59.02 | 229.4 |
| Crystallinity (%) | 40.9 | 42.1 | 78.1 |

The sutures were mechanically evaluated. The results are shown in FIGS. 4A-4B and FIG. 5. As seen in FIG. 4B, the HT suture was twice as strong as the normal tenacity (NT) at the same diameter.

In addition, the UHMWPE suture was used in the study to determine the integrity of the polymer base in comparison to see how high tenacity polyester will hold up (durability and strength) in chemical and mechanical testing. Referring to the results in FIG. 5, after evaluating the properties of the sutures, the sutures were then sterilized by exposing them to ethylene oxide in normal conditions, with gas at about 500 mg/L, temperature about 50 degrees C., RH 55% and exposure time about 3 hours. The sutures were then evaluated to determine how the polymers hold up (durability and strength) to a sterilization cycle.

The study demonstrated that UHMWPE is extremely strong with high stiffness. The high tenacity suture is much better than the normal tenacity suture because it higher in density and higher in tenacity making a stronger suture for the same suture diameter. The device or material is best if it behaves like the part it is replacing in an in-vivo application. The high tenacity has better overall properties than the current regular tenacity expecting better results in long-term biostability—The high tenacity (HT PET) fiber in a suture form demonstrated that for strength to diameter it only takes two-thirds of regular tenacity fiber resulting in a thinner wall device.

According to an aspect of the invention, device thickness in accordance with the invention comprises a device constructed of a high tenacity micro fiber material that is less than 0.0025".

Example 2

Mechanical data of a final monofilament fiber was performed using a standard tensile tester with cord and yarn grips to hold the sample for testing. Gauge length was 254 mm, Crosshead speed was 300 mm/min, according to ASTM 2256-10. Results are demonstrated in Table 2 below.

TABLE 2

|  | Linear Density (den) | Elongation at Break (%) | Tenacity (gf/d) | Diameter (in) |
| --- | --- | --- | --- | --- |
| 1 | 5.4 | 6.8 | 6.89 | 0.0009 |
| 2 | 5.4 | 8.6 | 6.87 | 0.0009 |
| 3 | 5.4 | 8.4 | 6.97 | 0.0009 |
| 4 | 5.4 | 6.8 | 6.84 | 0.0009 |
| 5 | 5.4 | 11.1 | 6.87 | 0.0009 |
| 6 | 5.4 | 7.4 | 6.87 | 0.0009 |
| 7 | 5.4 | 8.3 | 7.05 | 0.0009 |
| 8 | 5.4 | 10 | 6.95 | 0.0009 |

TABLE 2-continued

|   | Linear Density (den) | Elongation at Break (%) | Tenacity (gf/d) | Diameter (in) |
|---|---|---|---|---|
| 9 | 5.4 | 8.1 | 7.07 | 0.0009 |
| 10 | 5.4 | 6.8 | 6.92 | 0.0009 |
|   | Avg: | 8.23 | 6.93 |   |
|   | SD | 1.43 | 0.08 |   |

Example 3

Mechanical data of a final multifilament fiber was performed using a standard tensile tester using cord and yarn grips to hold the sample. Gauge length was 254 mm. Crosshead speed was 300 mm/min, according to ASTM 2256-10. Results are demonstrated in Table 3 below.

TABLE 3

|   | Linear Density (den) | Elongation at Break (%) | Tenacity (gf/d) |
|---|---|---|---|
| 1 | 20 | 12.9 | 7.53 |
| 2 | 20 | 9.5 | 7.27 |
| 3 | 20 | 11.8 | 7.61 |
| 4 | 20 | 11.7 | 7.46 |
| 5 | 20 | 11.5 | 7.53 |
|   | Avg: | 11.48 | 7.48 |
|   | SD | 1.23 | 0.13 |

The tests, which are used in the discussion of the invention and examples were performed using ASTM D-2256-10 Standard Test Method for Tensile Properties of Yarns by the Single-Strand Method.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A sterilized implantable medical device comprising:
a fiber consisting essentially of high tenacity PET polymer having a denier per filament of less than 1.5 denier per filament (dpf), and a tenacity of from about 7.0 to 9.0 gram-force per denier.

2. The device of claim 1 wherein the fiber has a fiber denier of equal or less than about 40.

3. The device of claim 1 wherein the fiber comprises a monofilament fiber.

4. The device of claim 3 wherein the monofilament fiber has a dpf of about 0.6-1.5.

5. The device of claim 1 wherein the fiber comprises a multi-filament fiber.

6. The device of claim 5 wherein the multi-filament fiber has a denier per filament of about 5-40.

7. The device of claim 6 wherein the multi-filament fiber has an elongation of less than 15%.

8. The device of claim 1 wherein the polymer has a starting relative viscosity higher than 1.636 dl/g.

9. The device of claim 8 wherein the polymer has a starting relative viscosity of about about 1.995 dl/g-2.015 dl/g.

10. The device of claim 8 wherein the polymer has a starting relative viscosity of about_1.9dl/g-2.2 dl/g.

11. The device of claim 1 wherein the fiber is free of titanium dioxide.

12. The device of claim 1 wherein the fiber is a pure polymer.

13. The device of claim 1 wherein the medical device comprises a catheter.

14. The device of claim 1 wherein the medical device comprises a tubular member.

15. The device of claim 14 wherein the tubular member comprises a suture.

16. The device of claim 15 wherein the suture has a linear density of greater than 1500 denier and a modulus greater than 5.0 giga pascals (GPa).

17. The device of claim 1 wherein the device is a low-profile material having a fabric thickness of less than 0.002"inches.

18. A sterilized implantable medical device comprising:
a monofilament fiber consisting essentially of high tenacity PET polymer having a dpf of from about 0.6-1.5, and a tenacity of from about 6.5 to 9.0 gram-force per denier.

19. A sterilized implantable medical yarn comprising a plurality of fibers wherein each of the fibers consist essentially of a high tenacity PET polymer, and wherein each of the fibers have a dpf of less than 1.5 and a tenacity from about 7.0-9.0 gram-force per denier.

20. The medical grade yarn of claim 19 having a denier of equal or less than about 40.

21. The medical grade yarn of claim 19 wherein the fibers are monofilament fibers.

22. The medical grade yarn of claim 21 wherein the monofilament fibers have a dpf from about 0.6-1.5.

23. The medical grade yarn of claim 19 wherein the fibers are multifilament fibers.

24. The medical grade yarn of claim 23 wherein the yarn has a denier of from about 5-40.

25. The medical grade yarn of claim 24 wherein the multifilament fibers have an elongation of less than 15%.

26. The medical grade yarn of claim 19 wherein the polymer has a starting relative viscosity higher than 1.636 dl/g.

27. The medical grade yarn of claim 19 wherein the polymer has a starting relative viscosity of about 1.995 dl/g-2.015 dl/g.

28. The medical grade yarn of claim 19 wherein the polymer has a starting relative viscosity of about 1.9 dl/g-2.2 dl/g.

29. The medical grade yarn of claim 19 wherein the fibers are free of titanium dioxide.

30. The medical grade yarn of claim 19 wherein the fibers are formed of a pure polyester.

* * * * *